United States Patent [19]
Matsuoka et al.

[11] Patent Number: 5,248,486
[45] Date of Patent: Sep. 28, 1993

[54] DEVICE, AGENT AND PROCESS FOR MEDICAL WASTE STERILIZATION

[75] Inventors: Akira Matsuoka, 1-11, Takezono-machi, Ashiya-shi, Hyogo-ken; Koichi Mimura; Masayuki Matsumoto, both of Kobe; Masaru Matsunami, Ibigawa; Kozo Mizutani, Narashino; Minoru Okamura, Urawa; Kazuomi Sakai, Koga; Toru Yamakawa, Narashino, all of Japan

[73] Assignees: Akira Matsuoka, Ashiya; Nihon Health Science Ltd., Tokyo; Kawai Lime Industry Co., Ltd., Oogaki; Sumitomo Cement Co., Ltd., Tokyo, all of Japan

[21] Appl. No.: 983,609

[22] Filed: Nov. 30, 1992

Related U.S. Application Data

[60] Continuation of Ser. No. 739,352, Aug. 2, 1991, abandoned, which is a division of Ser. No. 510,224, Apr. 17, 1990, abandoned.

[30] Foreign Application Priority Data

| Apr. 17, 1989 | [JP] | Japan | 1-96639 |
| Apr. 17, 1989 | [JP] | Japan | 1-96640 |
| Aug. 31, 1989 | [JP] | Japan | 1-225554 |
| Dec. 12, 1989 | [JP] | Japan | 1-322244 |

[51] Int. Cl.$^5$ .................... A61L 2/00; A61L 9/00; F24J 1/00; C09K 3/18
[52] U.S. Cl. .................... 422/294; 422/26; 422/27; 422/28; 422/113; 422/295; 422/305; 422/307; 126/263 R; 252/70
[58] Field of Search .............. 422/27, 26, 28, 29, 422/32, 38, 102, 113, 118, 294, 295, 299, 301, 305, 306, 307; 126/263; 252/70

[56] References Cited

U.S. PATENT DOCUMENTS

| 3,653,372 | 4/1972 | Douglas | 126/263 |
| 3,675,637 | 7/1972 | Trimble | 126/263 |
| 3,766,079 | 10/1973 | Jackman et al. | 252/70 |
| 3,903,011 | 9/1975 | Donnelly | 126/263 |
| 3,942,510 | 3/1976 | Garrett | 126/263 |
| 3,970,068 | 7/1976 | Sato | 126/263 |
| 4,171,340 | 10/1979 | Nishimura et al. | 422/1 |
| 4,425,251 | 1/1984 | Gancy | 126/263 |

FOREIGN PATENT DOCUMENTS

004073  9/1979  European Pat. Off. .

Primary Examiner—James C. Housel
Assistant Examiner—Christopher Y. Kim
Attorney, Agent, or Firm—Armstrong, Westerman, Hattori, McLeland & Naughton

[57] ABSTRACT

A heat generating agent for medical waste sterilization. The agent is at least one compound selected from calcium oxide, calcined dolomite, and magnesium oxide, and at least one compound selected from sulfamic acid, sodium bisulfate, and anhydrous phosphoric acid. The present invention also provides a method for sterilizing medical wastes. The method includes the steps of subjecting medical waste to exothermic reaction between water and a heat generating agent selected from calcium oxide and calcined dolomite or to exothermic reaction between iron powder and oxygen to generate reaction heat and/or alkalinity by the exothermic reaction. The present invention provides an apparatus to be used according to the method mentioned above. The apparatus is constructed essentially of a partition for partitioning the container into the housing for housing medical waste and a housing for the exothermic reaction, contact for contacting the first exothermic material to the second exothermic material to react the first exothermic material with the second exothermic material, and a passage passing through the partition when the first exothermic material reacts with the second exothermic material.

10 Claims, 8 Drawing Sheets

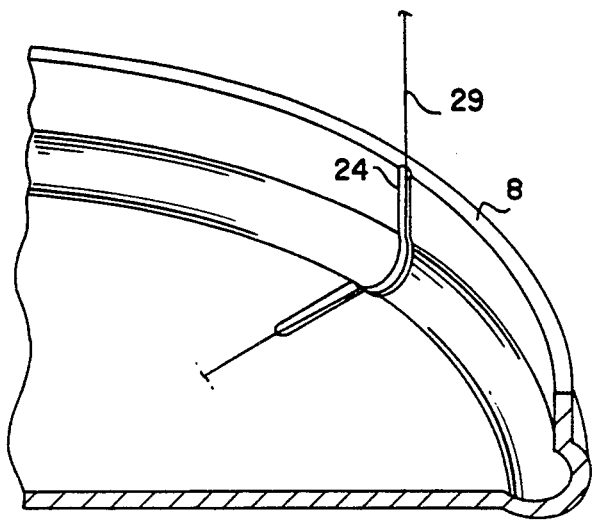
Fig.5
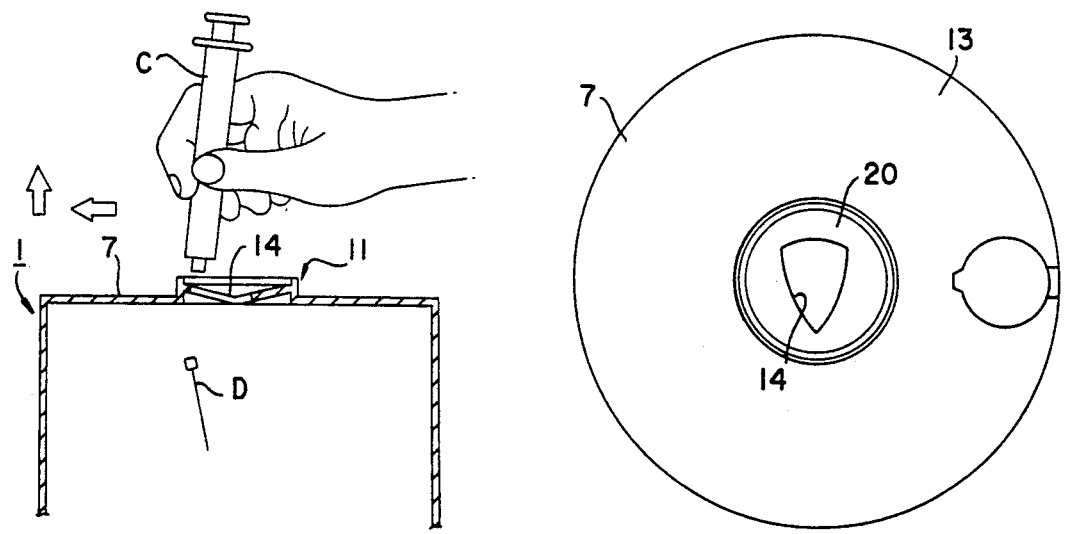
Fig.6
Fig.7

DEVICE, AGENT AND PROCESS FOR MEDICAL WASTE STERILIZATION

This application is a continuation of application Ser. No. 07/739,352 filed Aug. 2, 1991, abandoned which in turn was a division of application Ser. No. 510,224 filed Apr. 17, 1990, abandoned.

BACKGROUND OF THE INVENTION

1. Field of the Invention

The present invention relates to sterilization agents, methods and devices applicable to sterilization of used hypodermic needles, disposable surgical instruments, other blood and body fluids drawing and handling devices, disposable labware such as pipettes, etc. as well as many other disposable items that come into contact with body fluids and micro-organisms.

2. Prior Art

Many kinds of disposable devices such as hypodermic needles, surgical instruments, other blood and body fluids drawing and handling devices, labware such as pipettes, test tubes, etc. are being used increasingly in clinical and research medicine in order to diminish the possiblity of accidental infection. Sterilization of such devices after use is also important for their safe disposal.

According to the regulations of many jurisdictions, such devices must be sterilized by heat, filtering, irradiation, or by chemical agents prior to disposal. For sterilization of plastic materials, irradiation with $\gamma$ rays is recommended. For sterilizing devices made of metal or glass, high temperature steam in an autoclave is recommended. For sterilizing unwoven cloth, sterilizing gas such as ethylene oxide is recommended.

However, such methods are often cumbersome, requiring large, expensive sterilization devices. Moreover, these conventional methods require a considerable amount of manual labor, including handling of the items to be sterilized which entails infection risks to the workers involved.

SUMMARY OF THE INVENTION

In consideration of the above, it is an object of the present invention to provide a sterilization device, agent and method whereby safe, convenient, effective, and reliable disposal of medical wastes can be carried out, while minimizing human contact with the items to be sterilized.

According to an aspect of the present invention, there is provided a disposable sterilization device having a discarded hypodermic needle holding space which is heated by heat generated through a chemical reaction, while at the same time, the items to be sterilized contained therein are caused to be exposed to heated vapors containing anti-microbial substances. After the sterilization operation is completed, the apparatus and the sterilized contents may safely disposed of as a whole.

An other aspect of the present invention provides a disposable sterilization device additionally having a communicating means for allowing the discarded hypodermic needle holding space to communicate with a heat generating agent chamber, and means for minimizing temperature and pressure gradients so that the process of sterilization can be completely and uniformly carried out. Other aspects of the present invention provide sterilization agents and methods.

BRIEF DESCRIPTION OF THE DRAWINGS

FIG. 5 is a partial cross-sectional view illustrating a cord that passes through the interior of an outer container according to the embodiment of the present invention shown in FIG. 1.

FIG. 6 is a partial cross-sectional view illustrating the use of a sterilization device according to the present invention.

FIG. 7 is a plan view showing a modification of the sterilization device shown in FIG. 1.

DETAILED DESCRIPTION OF THE PREFERRED EMBODIMENTS

Figure 1:
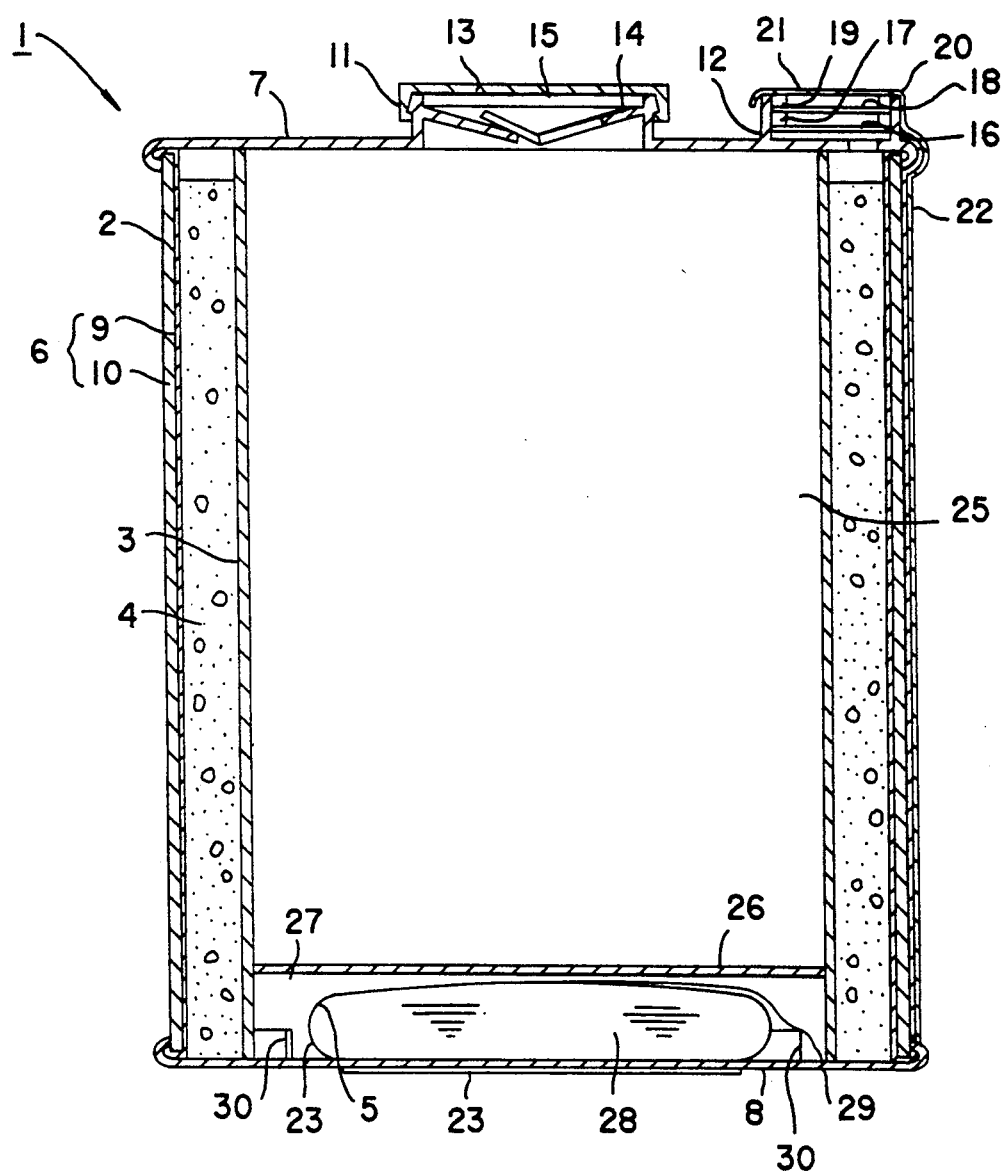
FIG. 1 is a schematic cross sectional view of a device for sterilization of discarded hypodermic needles according to a third embodiment of the present invention.

In the following sections the preferred embodiments of the present invention will be described in detail. To start with, a first preferred embodiment concerned with the sterilization heat generating agent (hereafter abbreviated as heat generating agent) of the present invention will be described.

The heat generating agents of the present invention constitute a dry phase, which when mixed with an aqueous phase which is physically partitioned from the dry phase until the time of reaction, generates heat whereby sterilization of medical waste is achieved. Heat generating agents which may suitably be applied to the dry phase heat generating agent of the present invention can be divided into two general groups, Group I and Group II. For Group I heat generating agents, as the principle agent, examples include one or two agents selected from the group including quicklime (calcium oxide), calcined dolomite, and magnesium oxide, optionally combined with a reaction moderating agent such as a Ca-Si compound. With such heat generating agents, together with providing a convenient and reliable heat source by virtue of their hydration reaction with added water, these agents pose little environmental risk when the reaction vessel and reagent remnants are later discarded after the sterilization process has been carried out. Furthermore, these types of heat generating agents can practically be employed in a powder, granular or pellet form. In particular, when quicklime is employed, the heat of its reaction with water can be increased by using a powder or finely granular material, for example a mixture of granular quicklime of which the particle diameter is on the order of 5 mm or less and quicklime powder, or granular quicklime material with particle diameters ranging from 1 to 5 mm is desirable. Additionally, material formed into pellets may be used as well, optionally combined with an inert binding agent in order to dampen the reaction with water somewhat and avoid the sudden generation of large amounts of heat in an uncontrolled fashion. Of course pure (or near pure) calcium oxide (CaO) can be used in place of quicklime, however in such a case as well, it is desirable to add a portion of an inert mineral substance, for example crushed limestone, or a Ca-Si compound or other reaction moderating agent in order to dampen the reaction with water somewhat. Further, powdered quicklime mixed with a retarding agent and pressed into grains or pellets may be used. When calcined dolomite is used, just as with quicklime, powdered or granular material, or powdered or granular material mixed with a reaction moderating agent may be used.

Optionally, an alkali neutralizing agent may be included to further facilitate the exothermic reaction, either dissolved in the aqueous phase or dispersed in the dry phase. For the alkali neutralizing agent, one or two compounds selected from the group including sulfamic acid, sodium bisulfate, and anhydrous phosphoric acid may be used. These alkali neutralizing agents act to combine with and at least partially neutralize alkali reaction products produced by the hydration reaction when the above described Group I agents mix with the aqueous phase, generating additional heat by the exothermic neutralization reaction in the process. It is acceptable to dissolve these alkali neutralizing agents in the aqueous phase, or they may be in a powdered or granular form, a mixture thereof, or as pellets, and may be mixed with the above described dry phase.

As previously mentioned, the exothermic reaction created in the present invention is achieved by mixing the above described dry phase with an aqueous phase. The aqueous phase employed is physically partitioned from the dry phase until it is desired to carry out the exothermic reaction. The aqueous phase may be water alone, or as mentioned above, can be an aqueous solution of one or more of the above mentioned alkali neutralizing agents.

Additionally, one or two reaction moderating agent selected from the group including magnesium chloride, calcium chloride and gypsum may be employed. These agents serve to moderate both the above described hydration reaction and alkali neutralization reaction, whereby both the time course and the temperature of the composite reactions can be controlled. These reaction moderating agents may be included with the dry phase, or optionally dissolved or suspended in the aqueous phase to form an aqueous solution or an aqueous slurry.

For a heat generating agent including a mixture of one or more Group I agents and alkali neutralizing agents, an approximately molar equivalent ratio is preferable, particularly, such a ratio so that after completion of the hydration and neutralization reactions, the pH of the aqueous phase is in the range of 6.0-8.5, or more preferably, in the range of 6.5-8.0.

Based on whether a system is provided in which the Group I heat generating agents are simply mixed with water, thereby generating heat through a single stage hydration reaction, or whether the system is provided further with a alkali neutralizing agent, thereby creating a second exothermic step of neutralization of alkali formed in the hydration step, thus creating a faster rate of temperature increase, greater maximum temperature, and a more sustained elevated temperature, it is possible to optimize the sterilization conditions for the type of medical waste to be disposed. Additional control is possible through inclusion of the above described moderating agents, inert substances, etc..

As mentioned above, the heat generating agents which may suitably be applied to the dry phase heat generating agent of the present invention can be divided into two general groups, Group I and Group II. For Group II heat generating agents, as the principle agent, a mixture including a first component of Portland Cement clinker mineral which is composed of solid solutions from the group of solid solutions including $3CaO.SiO_2$ solid solution, $2CaO.SiO_2$ solid solution and $2CaO.Fe_2O_3—6CaO.2Al_2O_3.Fe_2O_3$ solid solutions; a second component including at least one compound selected from the group including $11CaO.7Al_2O_3.CaX_2$ (here X indicates a halogen atom), $12CaO.7Al_2O_3$, $CaO.Al_2O_3$, $3CaO.3Al_2O_3.CaSO_4$ and $3CaO.3Al_2O_3.CaF_2$; and a third component including at least one material selected from the group including anhydrous gypsum, hemihydro-gypsum and dihydro-gypsum.

With such Group II heat generating agents, a ratio by weight of the first component to the second component of in the range of 1:99 to 99:1, and a ratio by weight of the sum of the first component and the second component to the third component of in the range of 100:3 to 1:34 is desirable. For the second component, either crystalline material, non-crystalline material, or a combination of both can be used.

When such Group II heat generating agents react with water, the second component immediately dissolves in the water, and then reacts with calcium hydroxide formed by the calcium silicate phase solution of the first component nearly immediately, thereby forming calcium aluminate—calcium sulfate hydration products, through which process heat of hydration is released. The amount of heat generated by this hydration process can be appropriately controlled by adjusting the amount of water and the three components making up the heat generating agent, and particularly, by adjusting the ratios of the three components making up the heat generating agent. For example, by appropriately adjusting the amount and ratios, it is possible to achieve a temperature of 90° C. or more sustained for at least seven minutes, or a temperature of 60° C. or more sustained for at least thirty minutes.

Additionally, depending on the ion concentration of the aqueous phase, the hydration products formed when the Group II agents react with water convert to various intermediate products which then rapidly aggregate, the aggregates having a microstructure to which any micro-organisms and other biological products present tend to adhere, thereby limiting the dispersion of microbes and noxious odors in exhaust gases.

If a fourth component is included with the heat generating agent which includes a suitable amount of one or more compounds from the group including the sulfates, nitrates, and carbonates of sodium, potassium, calcium, aluminum, iron, manganese, and magnesium, as well as composite compounds thereof, the speed of formation of the above mentioned aggregates can be controlled, these aggregates composed essentially of iron (I) sulfate, iron (II) sulfate, aluminum sulfate, alum compounds, calcium carbonate, manganese sulfate, aluminum nitrate, sodium sulfate, potassium sulfate and the like. When this fourth component is included, it is desirable that the ratio by weight of the sum of the first, second and third components to that of the fourth component is 5:1 or greater.

Additionally, if a fifth component is included with the heat generating agent which includes a suitable amount of one or more compounds from the group including oxycarboxylic acid, carboxylic acid and their salts, the speed of formation of the above mentioned aggregates can additionally be controlled. When this fifth component is included, it is desirable that the ratio by weight of the sum of the first, second, third and fourth components to that of the fifth component is 10:1 or greater.

For all of the various above described components, the materials used can be in the form of powders, particles, mixtures thereof, or as pellets.

In the following section a second preferred embodiment of the present invention will be described concerning the sterilization method of the present invention.

In the method of the present embodiment, used hypodermic needles, disposable surgical instruments, other blood and body fluids drawing and handling devices, disposable labware such as pipettes, etc. as well as many other disposable (not reusable) items that come into contact with body fluids and micro-organisms may be suitably sterilized so that they may be safely discarded. In order to sterilize such items, using a sterilization device into which the items to be sterilized have been deposited, and which has been charged with a Group I heat generating agent as described in the first preferred embodiment, for example quicklime (calcium oxide), calcined dolomite, magnesium oxide or a mixture thereof, water is brought into contact with the above mentioned Group I heat generating agent whereby an exothermic hydration reaction is initiated and allowed to continue.

By virtue of the above mentioned exothermic hydration reaction, heat is generated, thereby heating the items to be sterilized, thus effecting sterilization. The amount, rate and length of heat generation is controlled by the type of heat generating agent, its state (i.e. powdered, granular, pellet form), amount, constitution (purity), as well as the amount of water supplied and other variables. Ideally, conditions are controlled so that the items to be sterilized are exposed to a temperature of on the order of 40° to 600° C., or more preferably of 50° to 350° C. The duration of heating should generally be controlled so as to last from 1 to 90 minutes, depending on the nature of the items to be sterilized.

With the hydration reaction of Group I heat generating agents, because the pH of the reaction mixture increases as the hydration reaction proceeds, alkali bearing steam is caused to be generated which further adds to the antimicrobial killing effected by the generated heat as these vapors come into contact with items to be sterilized.

Further, when the Group I heat generating agents are employed, and further, when an alkali neutralizing agent is included, an exothermic alkali neutralization reaction occurs in addition to the hydration reaction. Thus, at the expense of alkalinity, additional antimicrobial heat can be generated. In this case, the amount, rate and length of heat generation is controlled by the type of heat generating agent as well as by the type of the alkali neutralizing agent, that is, by their state (i.e. powdered, granular, pellet form), amount, constitution (purity), as well as the amount of water supplied and other variables.

By adding reaction moderating agents, the temperatures generated and the duration of heating can be further controlled to match the desired conditions. Thus, by adding, for example, calcium chloride or magnesium chloride to the principle heat generating agent (for example quicklime), after bringing water into contact with the heat generating agent, chloride ions are generated which tend to form a reaction layer on the surface of the heat generating agent which exerts a controlling effect. By adding gypsum, an integral control effect of gypsum itself can be achieved, which in turn remarkably enhances the controlling effect of the chloride ions. When these moderating agents, gypsum, etc. are provided dissolved in the added water or as a slurry therein, the control achieved tends to be much more uniform.

With the sterilization method of the present invention, when the two stage reaction procedure is employed, that is when the alkali neutralizing agent is employed in addition to the heat generating agent, a higher temperature of a longer duration can be achieved. Compared with conventional sterilization methods such as γ wave radiation, autoclaving (high pressure water vapor sterilization), exposure to ethylene oxide and other antimicrobial gases, etc., which require expensive equipment, by the method of the present invention, safe, effective, easy, convenient, reliable and inexpensive sterilization can be achieved.

In the case when heat generating agents from Group II are employed in the method of the present embodiment, just as when Group I agents are employed, using a sterilization device into which the items to be sterilized have been deposited, and which has been charged with the Group II heat generating agent, water is brought into contact with the above mentioned Group II heat generating agent whereby an exothermic hydration reaction is initiated and allowed to continue.

By virtue of the above mentioned exothermic hydration reaction, heat is generated, thereby heating the items to be sterilized, thus effecting sterilization. Hydration reaction products of the first and second components of the Group II heat generating agents cause the pH of the reaction mixture to increase as the hydration reaction proceeds. Thus, just as when the Group I agents are employed, alkali bearing steam is caused to be generated which further adds to the antimicrobial killing effected by the generated heat as these vapors come into contact with items to be sterilized. Moreover, intermediate products generated when the Group II heat generating agents react with water serve to absorb micro-organisms and biological substances, thus limiting scattering of the organisms or vile odors outside of the apparatus.

Just as when Group I heat generating agents are used, when Group II heat generating agents are employed, the amount, rate and length of heat generation is controlled by the type of heat generating agent, its state (i.e. powdered, granular, pellet form), amount, constitution (purity), as well as the amount of water supplied and other variables.

With the sterilization method of the present invention employing Group II heat generating agents, through the added effects of generated heat, alkaline vapors, as well as other reactive intermediates, an effective sterilization of various suitable items can be realized. Compared with conventional sterilization methods such as γ wave radiation, autoclaving (high pressure water vapor sterilization), exposure to ethylene oxide and other antimicrobial gases, etc., which require expensive equipment, by the method of the present invention, safe, effective, easy, convenient, reliable and inexpensive sterilization can be achieved.

With the method of the present embodiment, rather than using Group I or Group II heat generating agents, when iron powder which is caused to react with air, or purer forms of oxygen, a quite effective thermal sterilization can be realized. With such a method, the temperature and length of reaction can be suitably controlled by adjusting the size of the iron powder particles.

In the following section a third preferred embodiment of the present invention will be described with reference to FIGS. 1 to 5.

In FIG. 1, a suitable example of a vessel for sterilization of discarded hypodermic needles by the method of the present invention is shown. As shown in the diagram, the basic structure of sterilization device 1 includes an outer container 2, an inner container 3 accommodated within outer container 2, a heat generating agent 4 provided in the space formed between outer container 2 and inner container 3, and a water bag 5 provided below inner container 3.

As shown in FIG. 1, outer container 2 is further made up of a cylindrical midsection 6, an upper cap 7 for sealing the upper opening of outer container 2, and a lower cap 8 for sealing the lower opening of outer container 2. The outer surface of the above mentioned midsection 6 is made of steel and is covered with a heat insulating material 10 such as cardboard.

Figure 2:
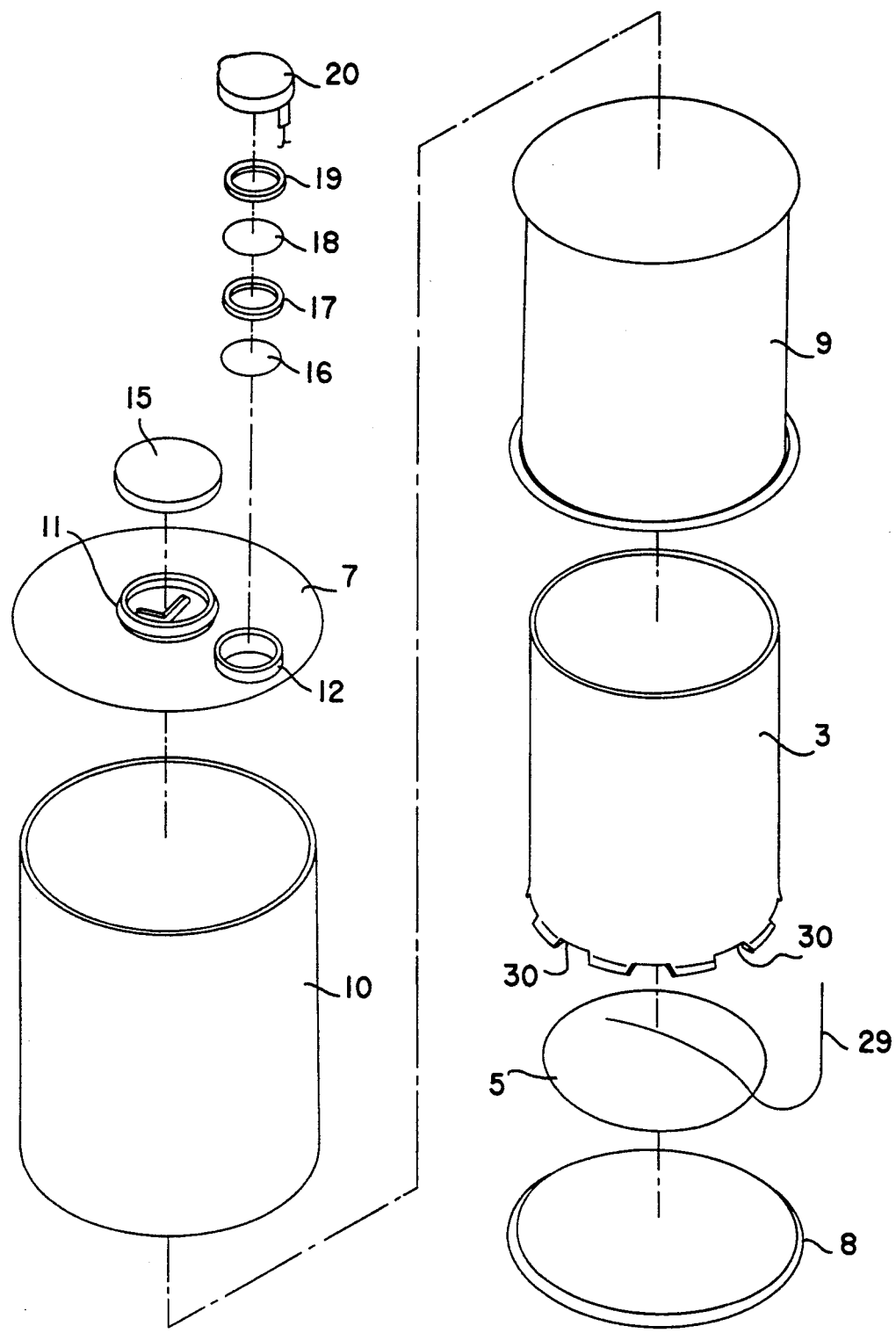
FIG. 2 is an oblique schematic disassembled view of the sterilization device shown in FIG. 1.
Figure 3:
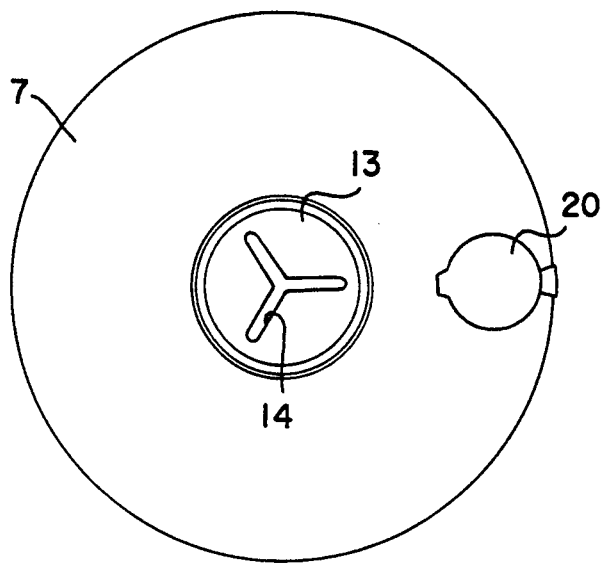
FIG. 3 is a overhead plan view of the sterilization device shown in FIG. 1.

As shown in FIGS. 1 and 2, a centrally located hypodermic needle disposal port 11 and a more peripheral exhaust port 12 are formed in the above mentioned upper cap 7. Upper cap 7 can be made of a composite resin, steel, or other metallic materials. The above mentioned hypodermic needle disposal 11 is cylindrically shaped and projects above the sterilization device 1. The internal portion of hypodermic needle disposal opening 11 is provided with a unitary plate formed shield 13 by which means the central opening formed therein is covered. As shown in FIG. 3, the above mentioned shield 13 is provided with a needle extractor slot 14 formed as a Y-shaped opening. A threaded needle disposal port cap 15 is provided which can easily be screwed on and off of the hypodermic needle disposal port 11 which is threaded on its external surface, thereby constituting a removable cover for the hypodermic needle disposal port 11. The above mentioned exhaust port 12 which is formed in the upper cap 7 projects above the sterilization device 1 in a relatively peripheral position, and is continuous with the space formed between outer container 2 and inner container 3. During sterilization, heat and generated steam is exhausted through the exhaust port 12. As shown in FIG. 2, a microbe-barrier filter 16 for preventing the escape of micro-organisms with the exhaust gasses, a retaining ring 17, a deodorizing membrane 18, and a second retaining ring 19 are successively provided one on top of another within the exhaust port 12, over which a safety seal 20 is affixed as shown in FIG. 4.

Figure 4:
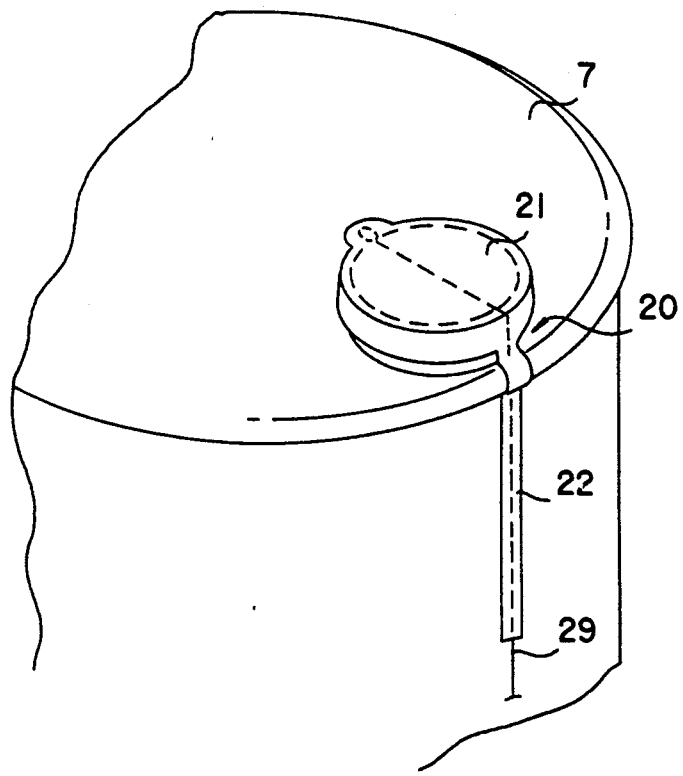
FIG. 4 is a partial perspective view illustrating a safety seal affixed to an exhaust port according to the embodiment of the present invention shown in FIG. 1.

As shown in FIG. 4, safety seal 20 consists of a sealing cap 21 which provides an air-tight seal for exhaust port 12, and an elongated strip 22 which extends from one side of the sealing cap 21 and trails over the top of upper cap 7 towards the upper edge of the sterilization device 1, and then downward along the outer surface of midsection 6 of outer container 2 to which it is affixed in a vertical orientation. As will be explained further on, the above described strip 22 which is affixed to the side of midsection 6 of outer container 2 functions as an opening cord for water bag 5.

The above mentioned microbe-barrier filter 16 is formed of poly-tetrafluroethylene (commercially available as Teflon) mesh having a pore diameter of no greater than 0.25 $\mu$m, by which means micro-organisms are prevented from scattering in the atmosphere with the exhaust gases from exhaust port 12. The above mentioned deodorizing membrane 18 is fabricated from sheet form lime felt, silica gel impregnated felt and the like, furthermore incorporating carbon fabric, whereby odors caused by steam generated from blood products and the like adherent to the hypodermic needles are prevented.

Lower cap 8 forms the lowermost surface of the sterilization device 1. On the external surface of lower cap 8, a sticker 23 which is gummed on both of its surfaces is affixed. By means of the above mentioned sticker 23, the sterilization device 1 can be anchored to whatever surface it is placed on, for example a laboratory counter, whereby toppling and sliding of the sterilization device 1 is prevented. As shown in FIG. 5, a groove 24 is formed in the inner surface of the edge of lower cap 8, whereby the interior of outer container 2 communicates with the exterior, and through which a cord passes as will be described further on.

Inner container 3 communicates with the above mentioned hypodermic needle disposal port 11 and is in the form of a cylinder having a bottom 26 which is inset somewhat, whereby a water bag accommodating space 27 is created beneath the lowermost surface of the bottom 26 and a discarded hypodermic needle holding space 25 is formed above the bottom 26 wherein the hypodermic needles to be sterilized are discarded through hypodermic needle disposal port 11. Additionally, inner container 3 serves to form a partition whereby water and the heat generating agent 4 to be described later are excluded from within inner container 3 prior to the sterilization operation. Inner container 3 is fabricated of polypropylene, polystyrene, polyethylene or some similar material which melts easily at the reaction temperature of the heat generating agent 4 and water and thus becomes permeable. In the present example, polypropylene has been employed.

The above mentioned water bag 5 is accommodated in the above described water bag accommodating space 27 formed below the bottom 26 of inner container 3. Water bag 5 is fabricated of a water impermeable composite resin material such as polyethylene, and as the name implies, is filled with water 28. The lower surface of water bag 5 which is adjacent to the above described bottom 26 includes a water discharge hole (not shown in the drawings) which is closed with a seal (not shown in the drawings) affixed thereon. One end of cord 29 is attached to the seal. This cord 29 passes through the bottom part of the sterilization device 1 running through the previously described groove 24 of lower cap 8, up the outer surface of outer container 2 to which it is attached, and then runs under the previously described strip 22 of safety seal 20 which is also affixed to the outer side of outer container 2, and finally connects with the sealing cap 21 of safety seal 20. The groove 24 of lower cap 8 is packed with grease or some material whereby an airtight seal is obtained.

Constructed as described above, a mechanism for bringing the heat generating agent 4 and water 28 into contact is created. By pulling on cord 29, the above described seal is torn of the water discharge hole, thereby releasing the water 28 contained within water bag 5. Further, as shown in FIG. 2, a plurality of notches 30 for exhausting water are formed in the lowermost end of inner container 3, through which the water 28 released from water bag 5 can flow outside of inner container 3.

As mentioned previously, a heat generating agent 4 fills the space formed between outer container 2 and inner container 3. For the heat generating agent 4, unadulterated quicklime, calcined dolomite, or a mixture containing these as the main components can be used. These components can be in the form of powder, grains, or otherwise as suit the needs of the implementation. In particular when quicklime is employed, the heat of its reaction with water can be increased by using a powder or finely granular material, for example a mixture of granular quicklime of which the particle diameter is on the order of 5 mm or less and quicklime powder, or granular quicklime material with particle diameters ranging from 1 to 5 mm is desirable. Additionally, material formed into pellets may be used as well. Of course pure (or near pure) calcium oxide (CaO) can be used, however with such a heat generating agent 4, it is desirable to add a portion of an inert mineral substance, for example crushed limestone, or a Ca-Si compound or other reaction moderating agent in order to dampen the reaction with water somewhat. Further, powdered quicklime mixed with a retarding agent and pressed into grains may be used. When calcined dolomite is used, just as with quicklime, powdered or granular material, or powdered or granular material mixed with a reaction moderating agent may be used. In the present preferred embodiment, quicklime and crushed lime stone mixed in a ratio of 7:3 by weight, the particle size controlled at between 1 to 5 mm, has been used.

In the following section, the operation of the sterilization device 1 of the third preferred embodiment of the present invention described above will be explained with reference to FIG. 6.

When a hypodermic needle is to be discarded using the apparatus of the present invention, first of all the needle disposal port cap 15 is removed and holding the cylinder of the hypodermic syringe, the needle attached thereto is inserted into the needle extractor slot 14 of hypodermic needle disposal port 11. After the needle is inserted into the central portion of the needle extractor slot 14 up to the base of the syringe cylinder, the hand held syringe cylinder is moved slightly laterally, whereby the nipple of the syringe (the mounting portion for the needle) is engaged in one of the legs of the Y-shaped needle extractor slot 14 between the hub of the needle and the base of the syringe. By then pulling the cylinder of the hypodermic syringe away from the needle extractor slot 14, the needle D is pulled away from the syringe C, after which the separated needle falls into the discarded hypodermic needle holding space 25 of inner container 3, as is shown in FIG. 6. Repeating the above process any number of times, the hypodermic needle holding space 25 of inner container 3 eventually fills with the collected needles which may then be safely disposed of after the sterilization process to be described below is carried out.

For the sterilization process, after the needle disposal port cap 15 is first secured on the hypodermic needle disposal port 11 of sterilization device 1, safety seal 20 is torn away thereby opening exhaust port 12 and cord 29 is pulled, thereby causing the water 28 to flow out of water bag 5. Then the water 28 flows out of the inner container 3 through the notches 30 and then mixes with heat generating agent 4 contained in the space between inner container 3 and outer container 2. Upon contact with the the released water 28, the heat generating agent 4 and water 28 react, thereby generating heat, and accordingly, heating the inner container 3. When the water 28 is first released from the water bag 5, the water 28 initially reacts with the heat generating agent 4 filling the lower part of the sterilization device 1. As the reaction further proceeds, the heated water 28 permeates throughout the heat generating agent 4 up to its uppermost portions, the reaction thereby continuing. Furthermore, steam generated in the course of the reaction passes upward through the heat generating agent 4 further facilitating the exothermic reaction therewith.

As the above described reaction process proceeds, the temperature elevates and the polypropylene inner container 3 begins to melt, whereby holes are formed at portions thereof allowing the space containing the discarded hypodermic needles and that containing the heat generating agent 4 to communicate. In this way, discarded hypodermic needles that were contained within the inner container 3 are sterilized. In the process, steam is generated with which alkali material contained in the heat generating agent 4 mixes to form a mist, this alkali mist then flowing through the discarded hypodermic needles in the inner container 3 coming into direct contact therewith, thus further enhancing the heat sterilization.

A portion of any pathogenic organisms present on the discarded hypodermic needles will tend to travel with the steam which is exhausted through exhaust port 12, but these micro-organisms will be trapped by the microbe-barrier filter 16, whereby steam free of pathogenic organisms can be safely discharged, and the micro-organisms are contained within the sterilization device 1 and killed therein. In a similar way, any objectionable odors generated by vaporization of blood products adherent the needles is trapped by the deodorizing membrane 18.

With the above described hypodermic needle discarding process, a used hypodermic needle can easily be removed from a syringe and dropped into the discarded hypodermic needle holding space 25 without requiring any direct contact of the operators hand with the needle itself. Furthermore, using the above described sterilization device 1 and sterilization process, any pathogenic organisms which may be adherent to the needles can be effectively killed, while at the same time, scattering of micro-organisms in the atmosphere and the generation of noxious odors is reliably prevented. Moreover, safety is enhanced as there is no need for poisonous gases and the like. Further, since the sterilization device 1 as a whole and the sterilized used needles contained therein can be safely discarded, the convenience of used hypodermic needle disposal is considerably enhanced.

In the above described third preferred embodiment of the present invention, the needle extractor slot 14 of hypodermic needle disposal port 11 is in the form of a Y as is shown in FIG. 3. The invention is not so limited however, however, and it is possible to employ the more widely opened, approximately triangle shaped needle extractor slot 14 shown in FIG. 7.

Further, in the present preferred embodiment, a heat generation mechanism is used employing water contained within water bag 5 which can be mixed at will with a particulate material which reacts exothermically with the water by pulling on the cord 29. Again however, the invention is not so limited and other conventional heat generating mechanisms can be employed, for example reacting iron powder with oxygen.

Also, in the present preferred embodiment, an inner container 3 which melts at the reaction temperature of the heat generating agent 4 and water has been employed, thus permitting admixture of the reaction mixture and vapors therefrom with the used needles within the discarded hypodermic needle holding space 25. However, rather than using a material that melts, is is also possible to employ one or more openings which are closed with a removable seal, as with the water bag 5, which can be torn away at the time of sterilization.

Further, as described above, the sterilization device 1 of the present embodiment has been employed for sterilizing used hypodermic needles, however the invention is not so limited and may be used equally well for sterilizing disposable surgical instruments, other blood and body fluids drawing and handling devices, as well as disposable labware such as pipettes, etc.

In the following section, a fourth preferred embodiment of the invention will be explained with reference to FIGS. 8 to 13.

Figure 8:
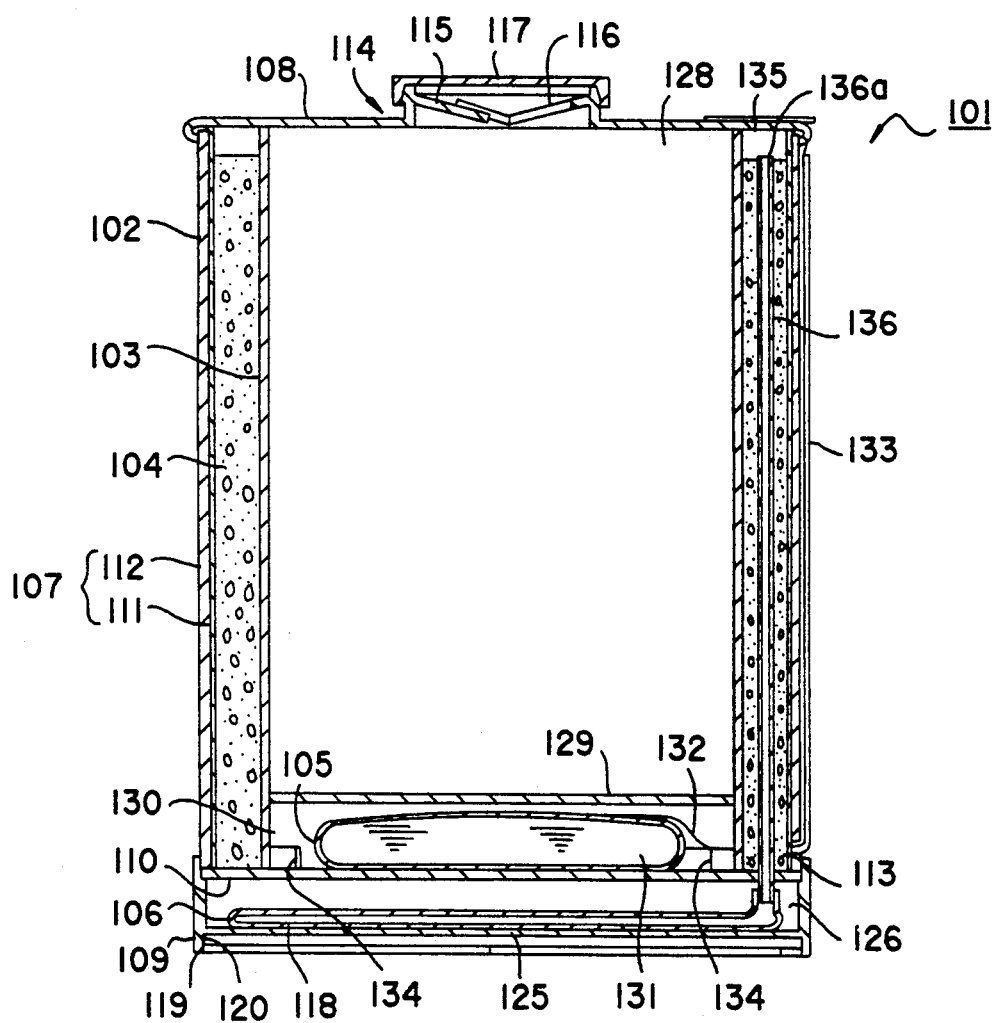
FIG. 8 is a schematic view of a device for sterilizing used hypodermic needles.

In FIG. 8, a suitable example of a sterilization vessel of discarded hypodermic needles by the method of the present invention is shown. In FIG. 8, a sterilization device 101 comprises an outer container 102, an inner container 103, a heat generating agent 104 provided in a space formed between outer container 102 and inner container 103, a water bag 105 provided below inner container 103, and an expanding air-containing bag 106 provided beneath this water bag 105 via a partition.

Outer container 102 comprises cylindrical drum 107, disc shaped upper cap 108, which is sealed onto the upper opening of this, cylindrical-form lower cap 109 which has a bottom, is attached to the lower edge of drum 107, and is sealed to the lower opening of drum 107, and dividing plate 110 which divides drum 107 and lower cap 109 in an airtight manner. Drum 107 is encased on the outer circumference of steel main body 111 by heat insulating materials 112 of cardboard, and the like. A groove 113 is provided in the lower edge of drum 107 which communicates the inside and outside of outer container 102, and a string described below passes through this groove 113.

Figure 9:
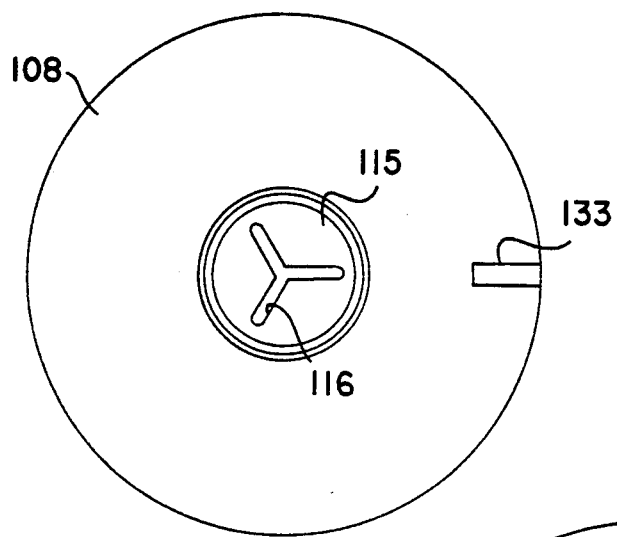
FIG. 9 is an exploded view of the device shown in FIG. 8.

Hypodermic needle disposal port 114 is provided in the center of upper cap 108. Upper cap 108 and the aforesaid lower cap 109 are made of compound resins or metals such as steel or iron to which heat insulating materials such as cardboard, and the like, have been bonded. Hypodermic needle disposal port 114 is a cylindrical object placed in a projecting fashion on the outside of sterilization device 101; on the inside of this an opening covered by a plate shaped body 115 is generally provided. As FIG. 9 shows, needle extraction slot 116 is formed in the center of plate body 115 from Y-shaped openings which radiate in three directions from the center. Furthermore, disposal port cap 117 is screwed onto the outer circumference of hypodermic needle disposal port 114 in a freely removable fashion, and by means of this needle extraction slots 116 can be sealed in an airtight fashion.

Figure 10:
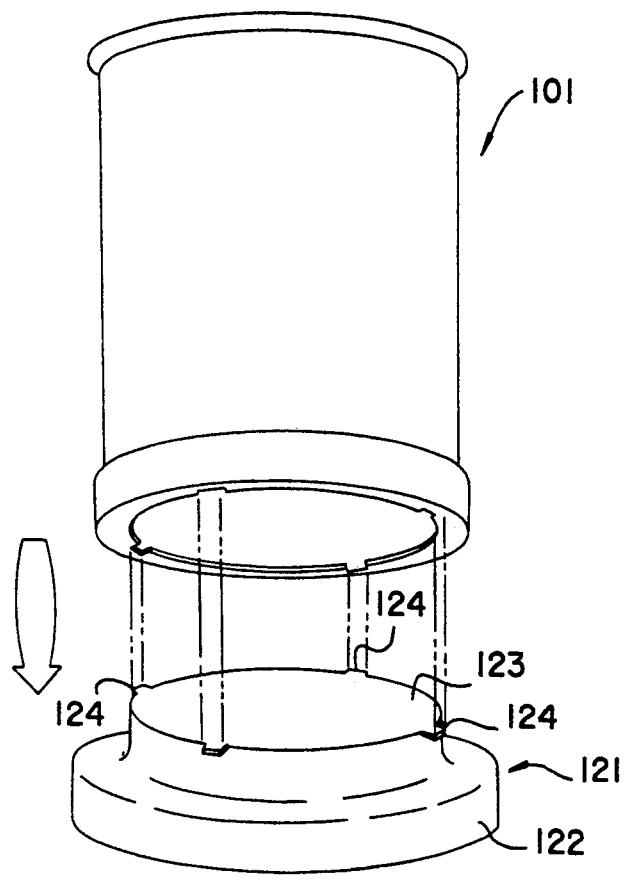
FIG. 10 is a perspective view of the device shown in FIG. 8.

Lower cap 109 forms a bottom surface 118 of the bottom of sterilization device 101; beneath the circumferential edge of bottom surface 118, locking ring 119 is provided in a projecting manner, and on the interior side of this locking ring 119 ring grooves 120 are provided. As is shown in FIG. 10, ring groove 120 is for the purpose of gripping stand 121, which fixes sterilization device 101. Gripping stand 121 is constructed of metal and comprises large-diameter disc shaped base 122, small-diameter disc shaped support element 123 which is provided above base 122, and a number of locking projections 124, . . . , which are provided around the circumference of support element 123 and which lock into the aforesaid ring grooves 120. Stand 121 possesses sufficient weight to fix sterilization device 101 in a stable manner when attached to it, and prevents sterilization device 101 from falling over. Furthermore, as FIG. 8 shows, hole 125, which communicates the inside of lower cap 109 and the area outside of sterilization device 101, is provided in bottom surface 118 of lower cap 109.

Within lower cap 109, expanding air-containing chamber 126 is provided separated from the interior side of drum 107 in an airtight fashion by means of dividing plate 110. Within this expanding air-containing chamber 126, expanding air-containing bag 106, which is made of flexible compound resins, etc., is inserted in a limp condition. Dividing plate 110 is made of rigid materials such as steel plates so that it will have sufficient strength to separate the interior of drum 107 and expanding air-containing chamber 126 in an airtight fashion. Expanding air-containing chamber 126 is made to receive the expanding air or generated water vapor which results from the generation of heat when medical waste disposal such as that described below is carried out. Therefore, expanding air-containing chamber 126 has a volume which is roughly 20–30% of the combined volume of the hypodermic needle receptacle and the heat generating agent container.

Inner container 103 has a cylindrical form with a bottom and is so arranged that it communicates with the aforesaid hypodermic needle disposal port 114, and has a raised bottom, so that it is placed above dividing plate 110. Furthermore, this inner container 103 is used as discarded hypodermic needle holding part 128, which is for the purpose of holding the discarded hypodermic needles within the said inner container 103, and inner container 103 itself serves as the heat generating agent and partition against water described below. In addition, this inner container 103 is made of materials with a low melting point such as polypropylene, polystyrene, polyethylene, and the like, which are easily melted by the generation of heat at the time of the exothermic reaction between the heat generating agent and water and allow passage easily; in this case it is made of polypropylene.

Beneath the bottom 129 of this inner container 103 water bag accommodating part 130, which is for the purpose of accommodating the aforesaid water bag 105, is provided. Water bag 105 is a bag made of compound resins which are not water-permeable, such as polyethylene, and the like which is filled with water 131; on the surface of bottom 129 a drainage hole (omitted in the diagram) is provided, and to this drainage hole a covering seal is attached. One end of cord 132 is attached to the seal, and this cord 132 passes along the upper surface of dividing plate 110 and through groove 113 of drum 107; it then runs up the outer circumferential surface of outer container 102 and its other end reaches the circumferential edge of upper cap 108 and i attached there. The attachment of cord 132 to the outer circumferential surface of outer container 102 is accomplished by the sealing of the cord to outer container 102 by means of safety seal 133. Safety seal 133 is in the form of a strip running in the direction of the length of cord 132, runs along the outer circumferential surface of drum 107 in the direction of the height of the drum, and reaches upper cap 108, covering and attaching cord 132. Groove 113 of drum 107, through which cord 132 passes, is filled with grease, and the like, so that the airtight state of sterilization device 101 will be maintained. In addition, at the bottom edge of inner container 103 a number of drainage notches 134 which communicate water bag accommodating space 130 and the heat generating agent accommodating space described below are provided.

In the above construction, contacting means for contacting heat generating agent 104 to the water 131 stored within water bag 105 into contact is provided. Further, at the base of this construction, by means of the pulling of cord 132 and the tearing off of safety seal 133, that seal is torn from water bag 105, the drainage hole is opened, the water 131 within the bag flows out and exits to the outside of inner container 103.

Heat generating agent accommodating part 135 is provided in the space between outer container 102 and inner container 103 and this heat generating agent accommodating space 135 is filled with heat generating agent 104. For the heat generating agent 104, unadulterated quicklime, calcined dolomite, or a mixture containing these as the main components can be used. These components can be in the form of powder, grains, or otherwise as suit the needs of the implementation. In particular when quicklime is employed, the heat of its reaction with water can be increased by using a powder or finely granular material, for example a mixture of granular quicklime of which the particle diameter is on the order of 5 mm or less and quicklime powder, or granular quicklime material with particle diameters ranging from 1 to 5 mm is desirable. Additionally, material formed into pellets may be used as well. Of course pure (or near pure) calcium oxide (CaO) can be used, however it is desirable to add a portion of an inert mineral substance, for example CaSi compounds, in order to dampen the reaction with water somewhat. Further, powdered quicklime mixed with a retarding agent and pressed into grains may be used.

When calcined dolomite is used, just as with quicklime, powdered or granular material, or powdered or granular material mixed with a retarding agent such as an inert mineral substance may be used.

Further, in the present preferred embodiment, quicklime and crushed limestone mixed in a ratio of 7:3 by weight, the particle size controlled at between 1 to 5 mm, has been used.

In addition, a communicating pipe 136 made of metals, hard compound resins and the like is provided in heat generating agent accommodating space 135 buried in heat generating agent 104. This communicating pipe 136 passes through dividing plate 110 and extends into expanding air-containing chamber 126; one end of it is placed in the upper end of heat generating agent accommodating space 135 in the vicinity of upper cap 108, and the other end is in contact with the opening (not shown in the diagram) of expanding air-containing bag 106 and is so placed that it communicates with the said bag.

Within heat generating agent accommodating space 135, opening 136a of communicating pipe 136 is so placed that it is not buried in heat generating agent 104, and heat generating agent 104 is placed in heat generating agent accommodating space 135 in a dispersed manner so that vapor can flow easily through heat generating agent 104 from bottom to top.

Next the method of use of a sterilization device 101 having this construction will be explained.

Figure 11:
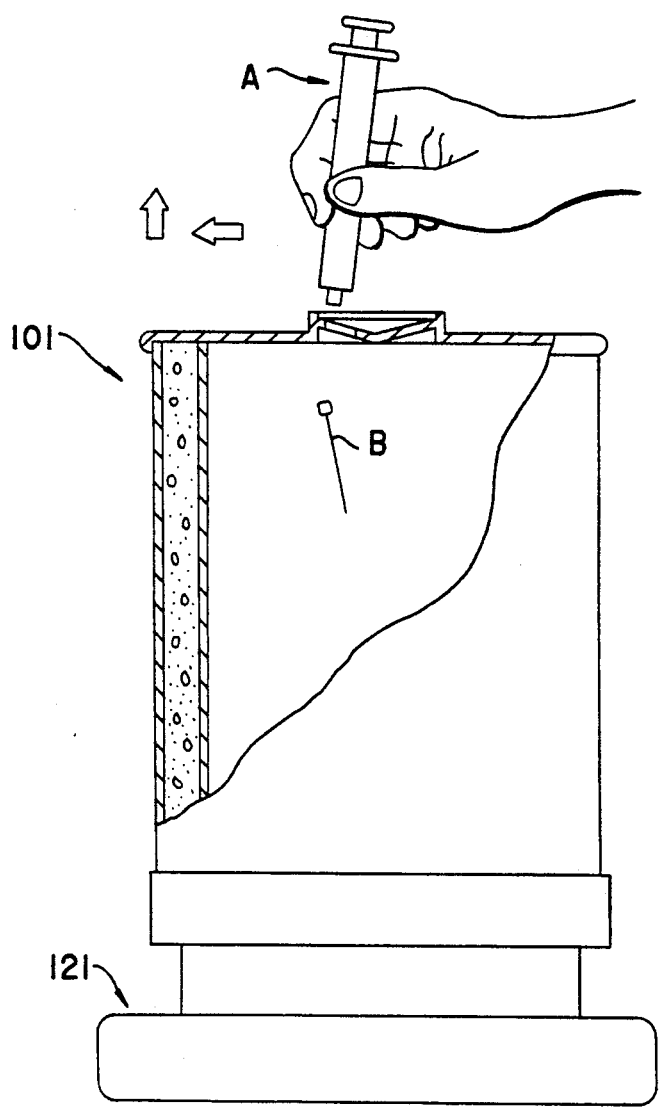
FIG. 11 is a partial cross-sectional view illustrating the use of the sterilization device shown in FIG. 8.

When a hypodermic needle is to be extracted, first of all the disposal port cap 117 is removed and holding the cylinder of the hypodermic syringe, the needle is inserted into needle extraction slot 116, and by catching the mounting portion for the needle in needle extraction slot 116, as FIG. 11 shows, needle B is separated from syringe cylinder A, and the separated needle B falls into discarded hypodermic needle holding space 128 of inner container 103. Repeating the above process any number of times, the discarded hypodermic needle holding space 128 eventually fills with the collected needles which may then be safely disposed of after the sterilization process to be described below is carried out.

For the sterilization process, after disposal port cap 117 is first secured on hypodermic needle disposal port 114, safety seal 133 is torn away and cord 132 is pulled, thereby causing the water 131 to flow out of water bag 105. Then the water 131 flows through the drainage notches 134 on the bottom edge of inner container 103 and reaches heat generating agent accommodating space 135 where it comes into contact and reacts with heat generating agent 104. Heat is generated by means of the reaction of heat generating agent 104 and water 131 and the heat in inner container 103 is increased. In this case, when the water 131 is first released from the water bag 105, it initially reacts with the heat generating agent 104 filling the lower part of the sterilization device 101. As the reaction further proceeds, the water permeates throughout the heat generating agent 104 up to its uppermost portions, the reaction thereby continuing. Furthermore, a part of the water 131 becomes steam as a result of the generation of heat by heat generating agent 104 and passes upward through heat generating agent 104 further facilitating the exothermic reaction therewith.

As the above described reaction process proceeds, the temperature elevates and the polypropylene inner container 103 begins to melt, whereby holes are formed at portions thereof allowing the discarded hypodermic needle holding space 128 and the space containing the heat generating agent 104 to communicate. In this case, as the reaction proceeds mainly on the lower side of heat generating agent accommodating space 135, the inner container 103 generally melts and holes open beginning with that side. Moreover, by means of the increase in temperature within inner container 103, the hypodermic needles that were contained within discarded hypodermic needle holding space 128 are sterilized. Furthermore, in the process steam is generated with which alkali material contained in the heat generating agent 104 mixes to form a mist, this alkali mist then flowing into discarded hypodermic needle holding space 128 and coming into direct contact with the hypodermic needles, thus further enhancing the heat sterilization.

Furthermore, within sterilization device 101 pressure is increased by means of the expansion of air caused by the heat-generating reaction as well as the generation of steam, however, this expanded air and steam flows through heat generating agent 104 and reaches opening 136a of communicating pipe 136, and passing through communicating pipe 136 flows into expanding air-containing bag 106 which is within expanding air-containing chamber 126. In this case, a portion of any pathogenic organisms present on the discarded hypodermic needles or foul smells will tend to travel with the expanding air or steam, but as this expanding air and steam flows into expanding air-containing bag 106, these pathogenic organisms or foul smells are also carried into expanding air-containing bag 106, and thus the escape of pathogenic organisms or foul smells to the outside of sterilization device 101 is completely prevented. The air within expanding air-containing chamber 126 is forced out under pressure from the expanded air, etc., within expanding air-containing bag 106 and exits to the outside of sterilization device 101 through hole 125 which is provided in lower cap 109. In this way, even if the expansion of air and generation of steam accompanying the generation of heat cause a buildup of internal pressure within sterilization device 101, through the medium of communicating pipe 136 the expanded air, etc., flows into expanding air-containing bag 106 and the air within expanding air-containing chamber 126 exits to the outside of sterilization device 101, and thus the buildup of internal pressure is moderated, so that a process of sterilization can be completely carried out using sterilization device 101.

With this type of construction of sterilization device 101, a used hypodermic needle can easily be dropped into the container without requiring any direct contact of the operators hand with the needle itself. Furthermore, a process of sterilization can be carried out with ease of operation while at the same time the diffusion of pathogenic microorganisms and foul smells can be prevented. Moreover, safety is enhanced as there is no need for poisonous gases and the like. Further, since the sterilization device 101 as a whole can be safely discarded after use, convenience is considerably enhanced.

Figure 12:
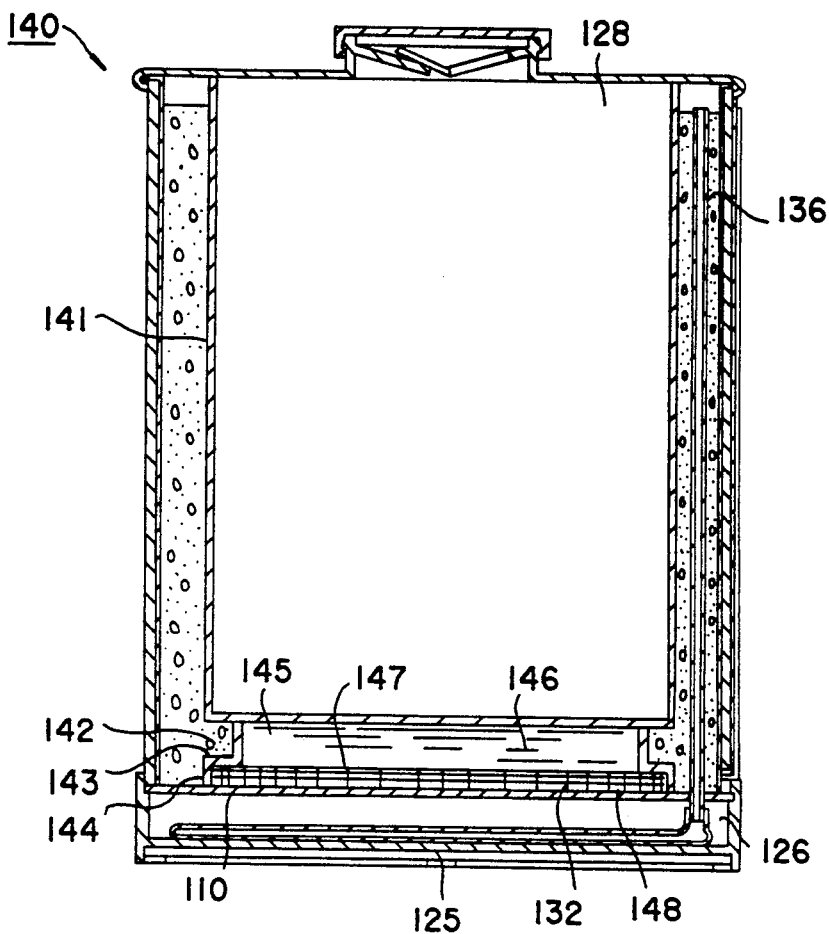
FIG. 12 is a partial cross-sectional view illustrating a sterilization device according to the fourth embodiment of the present invention.

FIG. 12 shows another example of the sterilization device for the disposal of used hypodermic needles. As the numbering of the essential parts of the construction is the same as that in FIG. 8, an explanation of this numbering will be omitted.

The differences between the sterilization device 140 shown in FIG. 12 and the sterilization device shown in FIG. 8 lie in the fact that instead of water bag accommodating space 130 and water bag 105, an accommodating space filled with water is provided.

In FIG. 12, inner container 141, which has a bottom and is cylindrical in shape, is provided within sterilization device 140, and on the bottom part of this inner container 141 a cylindrical-form cylinder 142 is provided which has a smaller interior diameter than the interior diameter of discarded hypodermic needle holding space 128. Supporting brim 143, which has a flat donut shape and the same outer diameter as the bottom surface of inner container 141 is provided parallel to the bottom surface of inner container 141, and on this supporting brim 143 a number of projections 144 . . . are provided along the circumferential edge of the brim, projecting downward and with a fixed spacing. The interior of cylinder 142 is accommodation space 145, which accommodates water, and this accommodation space 145 is filled with water 146. Furthermore, on the bottom surface of accommodation space 145 polyethylene sheet 147 is attached, and by means of this the water 146 held by accommodation space 145 is held in a watertight fashion. The end of cord 132 which is the opposite of the end of cord 132 which has been drawn out to the outside of sterilization device 140 is attached to polyethylene sheet 147. Below polyethylene sheet 147 and in the space between it and dividing plate 110, space 148, which is surrounded by projections 144, is provided. This space 148 communicates with heat generating agent accommodating space 135 through the medium of the spaces between projections 144, so that by means of this accommodation space 145 is connected with heat generating agent accommodating space 135 through the medium of polyethylene sheet 147 and space 148.

Even though sterilization device 140 has this type of construction, its operation is the same as that of sterilization device 101 shown in FIG. 8. In other words, in this sterilization device 140, by means of the pulling of the end of cord 132 which is on the outside of sterilization device 140, the polyethylene sheet 147 separates from supporting brim 143, and water 146 flows from accommodation space 145 through the spaces between projections 144 to heat generating agent accommodating space 135, where this water reacts with heat generating agent 104 and heats and sterilizes discarded hypodermic needle holding space 128.

Moreover, in this sterilization device 140 as well as in sterilization device 101 shown in FIG. 8, used hypodermic needle can easily be dropped into the container without requiring any direct contact of the operators hand with the needle itself. Furthermore, a process of sterilization can be carried out with ease of operation while at the same time diffusion of pathogenic organisms and foul smells to the outside of the container can be prevented, so that completeness and convenience are considerably enhanced.

Figure 13:
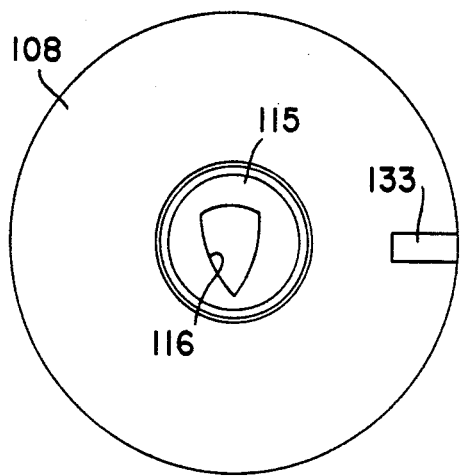
FIG. 13 is an overhead plan view of the device shown in FIG. 12.

In the aforesaid preferred embodiments, needle extraction slots 116 of hypodermic needle disposal port 114 were made Y-shaped notches running in three directions from the center as FIG. 9 shows, but this is not necessarily so restricted; for example, as is shown in FIG. 13, a notch in the form of a shortened triangle is possible.

Furthermore, in the aforesaid preferred embodiments, cord 132 was led to the outside by means of groove 113, but it is also possible to pass cord 132 through communicating pipe 136 and then pass it through upper cap 108 and so lead it to the outside.

In addition, the construction is not limited to that in which the device which allows penetration of the partition (in the aforesaid preferred embodiments, inner containers 103 and 141) between heat generating agent 104 and the water at the time of the generation of heat is the melting of inner container 103 (141) by means of the generation of heat, as in the aforesaid preferred embodiments; for example, an enclosing material could be provided beforehand in the inner container, and when the reaction is to begin (when sterilization is to begin) the said enclosing material could be removed.

Furthermore, in the aforesaid preferred embodiments, an example was given of an application in a sterilization device for the disposal and sterilization of used hypodermic needles, but this is not necessarily so limited; an application to a processing vessel covering general medical disposal, such as that of lancets, scalpels, laboratory dishes, pipettes, gauze, bandages, containers for holding blood products for transfusion, test tubes, specimen cups, laboratory animals, etc., is possible.

In addition, in the aforesaid preferred embodiments quicklime was used as a heat generating agent, but it is possible to use calcined dolomite or iron powder; in the case in which iron powder is used, air (oxygen) is used in place of water.

EXPERIMENTAL EXAMPLE 1

CaO and water were mixed to generate heat, and the sterilizing effects of the reaction against four different bacteria (*Staphylococcus aureus* [ATCC25923], *Escherichia coli* [ATCC25922], *Pseudomonas aeruginosa* [ATCC27853], and *Bacillus subtillis* [ATCC6633]) are examined as follows.

First, heat generating material CaO (150 g) and water (50 ml) separately retained in plastic bags, were together contained in an aluminum bag. The aluminum bag was retained in a thermally insulated box, then the bacteria were suspended in salt water, and the solution was strained through a sterilized gauze. The sterilized gauze was put on a sterilized glass plate. Then the plastic bag containing water was broken by force to liberate the water, and react the water with the CaO. Then the aluminum bag was opened. The glass plate on which the sterilized gauze was placed was put on the aluminum bag. The aluminum bag and the glass plate were retained in the thermally insulated box for 60 minutes. Then the gauze was taken out of the box and placed in an incubator to culture any surviving bacteria.

TABLE 1

| Microorganism | Control | Microorganism Concentration | |
|---|---|---|---|
| Staphylococcus aureus | (+) | Upper | $10^2$/ml (−), $10^5$/ml (−) |
| | | Middle | $10^2$/ml (−), $10^5$/ml (−) |
| | | Lower | $10^2$/ml (−), $10^5$/ml (−) |
| Escherichia coli | (+) | Upper | $10^2$/ml (−), $10^5$/ml (−) |
| | | Middle | $10^2$/ml (−), $10^5$/ml (−) |
| | | Lower | $10^2$/ml (−), $10^5$/ml (−) |
| Pseudomonas aeruginosa | (+) | Upper | $10^2$/ml (−), $10^5$/ml (−) |
| | | Middle | $10^2$/ml (−), $10^5$/ml (−) |
| | | Lower | $10^2$/ml (−), $10^5$/ml (−) |
| Bacillus subtillis | (+) | Upper | $10^2$/ml (−), $10^5$/ml (−) |
| | | Middle | $10^2$/ml (−), $10^5$/ml (−) |
| | | Lower | $10^2$/ml (−), $10^5$/ml (−) |

Table 1 shows that the four kinds of bacteria were all successfully destroyed. It seems that the bacteria are killed not only by the heat generated by the reaction of CaO and water, but also by the alkalinity of the solution.

EXPERIMENTAL EXAMPLE 2

A experiment similar to EXPERIMENTAL EXAMPLE 1 was performed with the exception that sintered dolomite was used instead of CaO. The experiment shows that all the four kinds of bacteria were successfully destroyed by these method. Therefore sintered dolomite and water are also effective for destroying these bacteria.

EXPERIMENTAL EXAMPLE 3

Temperature distribution created by a reaction between CaO and water was measured as follows.

First 150 g of CaO having a purity higher than 95% was retained in a steel vessel. Then 50 ml of water was added to the CaO. The temperature of the solution was measured. Table 2 shows the distribution in terms of time. Table 3 shows the results of a similar experiment wherein 40 ml of water was used.

TABLE 2

| | Vessel Section, degrees C. | | | |
|---|---|---|---|---|
| | Lowermost | Upper Lid | Central | Upper |
| Pre-reaction | 26 | 26 | 26 | 28 |
| Immediately After Reaction | 63 | 44 | 26 | 29 |
| 30 secs | 176 | 137 | 61 | 83 |
| 1 min | 236 | 203 | 78 | 86 |
| 2 min | 277 | 254 | 90 | 92 |
| 3 min | 284 | 267 | 116 | 98 |
| 5 min | 279 | 268 | 164 | 111 |
| 8 min | 254 | 250 | 180 | 127 |
| 10 min | 243 | 241 | 179 | 131 |
| 15 min | 230 | 228 | 176 | 137 |
| 20 min | 227 | 225 | 175 | 140 |
| 30 min | 218 | 217 | 170 | 139 |
| 40 min | 199 | 198 | 158 | 131 |
| 50 min | 174 | 172 | 142 | 123 |
| 60 min | 154 | 152 | 129 | 113 |
| 70 min | 128 | 127 | 111 | 100 |
| 80 min | 118 | 117 | 104 | 94 |

TABLE 3

| | Vessel Section, degrees C. | | | |
|---|---|---|---|---|
| | Lowermost | Upper Lid | Central | Upper |
| Pre-reaction | 26 | 26 | 26 | 28 |
| Immediately After Reaction | 64 | 73 | 35 | 67 |
| 30 secs | 126 | 105 | 55 | 69 |
| 1 min | 153 | 132 | 65 | 85 |
| 2 min | 186 | 166 | 100 | 97 |
| 3 min | 201 | 186 | 130 | 104 |
| 5 min | 213 | 199 | 147 | 108 |
| 8 min | 214 | 203 | 156 | 114 |
| 10 min | 210 | 203 | 161 | 121 |
| 20 min | 199 | 195 | 160 | 128 |
| 30 min | 182 | 180 | 151 | 127 |
| 40 min | 167 | 164 | 141 | 121 |
| 50 min | 149 | 147 | 128 | 112 |
| 60 min | 128 | 126 | 114 | 102 |
| 70 min | 116 | 115 | 105 | 95 |

TABLE 4

| Component 1 | | |
|---|---|---|
| $3CaO \cdot SiO_2$, 50.5 | $2CaO \cdot SiO_2$, 6.5 | $4CaO \cdot Al_2O_3 \cdot Fe_2O_3$ 4.7 |

| Component 2 | Component 3 | Total | Aqueous Solution Immediately After Mixing |
|---|---|---|---|
| $11CaO \cdot 7Al_2O_3 \cdot CaF_2$ 17.0 | $CaSO_4$ 16.0 | 94.7 | 12.0 |

Reagents were prepared as follows.

A composition of $CaCO_3$, bauxite, clay, and fluorite is ground and baked. The compositions shown with numbers 1 and 2 in Table 4 were obtained. The composition was again ground so that the powder was of 5,200 square cm per gram. Anhydrous plaster (containing 96.2% of $CaSO_4$) was also ground so that the surface area was 6,200 square cm per gram, and added to the compositions 1 and 2 above.

Sterilizing of the thus obtained agent against the above mentioned four kinds of bacteria was tested according to a method similar to that in EXPERIMENTAL EXAMPLE 1. It was found that all of the four kinds of bacteria were completely destroyed by the agent. The temperature in the vessel during the experiment was higher than 80 degrees C. for more than 6 minutes, and higher than 60 degrees C. for more than 30 minutes. In light of the fact that the AIDS virus is killed at a temperature of 58 degrees C. in 30 minutes, or at a temperature of 80 degrees C. in 5 minutes, this agent is effective against the AIDS virus. Similarly, the agent is effective against cancer viruses and hepatitis B.

EXPERIMENTAL EXAMPLE 5

CaO and an aqueous solution of sulfamic acid were reacted. The sterilizing effects of this reaction was tested against the four kinds of bacteria described above as follows.

CaO was retained in a plastic bag, and the sulfamic acid was retained in another plastic bag. The bags were retained in an aluminum bag. The aluminum bag was placed in a thermally insulated box. The bacteria were suspended in water, and the sterilized gauze was soaked in the resulting solution. Then the gauze was placed on a sterilized glass plate. The bags containing sulfamic acid and CaO were broken to release their respective substances. The aluminum bag was then broken. The glass plate whereon the gauze was placed was put on the aluminum bag. The aluminum bag and the glass plate were kept in the thermally insulated box for approximately 60 minutes. Then the gauze was placed in an incubator to culture any surviving bacteria. The result shows that all four kinds of bacteria were completely destroyed. This shows that the reaction of CaO and sulfamic acid is effective against the four kinds of bacteria.

EXPERIMENTAL EXAMPLE 6

Heat controlling effect of heat controlling agents was tested as follows.

85-55 unit weight of CaO, 10-40 unit weight of $CaCl_2$, and 5 unit weight of plaster was mixed. Then water was added to the mixture. The highest temperature was between 100 and 120 degrees C. Heat was generated during 4-5 minutes.

When water was added to CaO, the highest temperature was 300 degrees C. and heat was generated during 0.83 minutes.

85-55 unit weight of CaO, 10-40 unit weight of $CaCl_2$, and 5 unit weight of plaster were mixed. Then water was added to the mixture and the temperature was measured. The highest temperature was between 105 and 125 degrees C. Heat was generated for 5-8 minutes.

EXPERIMENTAL EXAMPLE 7

CaO was reacted with water in a vessel shown in FIG. 1, and the temperature was measured by changing the amount of water. Table 5 shows the test results. The temperature was measured around the heat generating agent (A) and in the agent (B).

TABLE 5

| CaO (g) | | | | | 100 | | | | | |
|---|---|---|---|---|---|---|---|---|---|---|
| Reaction Water (ml) | 16 | | 24 | | 32 | | 40 | | 48 | |
| Measured Temp. | A | B | A | B | A | B | A | B | A | B |
| Highest Temp. degrees C. | 140.3 | 229.0 | 153.0 | 247.0 | 161.3 | 260.4 | 145.0 | 342.7 | 141.0 | 262.7 |
| Temp. Retention Time mins. secs | | | | | | | | | | |
| Above 120° C. | 4.40 | 16.00 | 5.50 | 24.20 | 8.31 | 29.30 | 5.40 | 19.10 | 5.00 | 18.20 |
| Above 100° C. | 8.00 | 21.00 | 8.40 | 29.20 | 11.40 | 35.30 | 8.50 | 22.30 | 8.20 | 22.40 |
| Above 70° C. | 14.20 | 28.20 | 15.40 | 39.40 | 18.10 | 48.00 | 16.00 | 29.50 | 16.50 | 32.00 |

EXPERIMENTAL EXAMPLE 8

The amount of the heat generating agent (CaO) and water were varied and the temperature was measured around the heat generating agent.

TABLE 6

| CaO (g) | 150 | | 200 | |
|---|---|---|---|---|
| Reaction Water (ml) | 36 | 48 | 36 | 48 |
| Highest Temp. degrees C. | 124.7 | 130.0 | 175.3 | 151.3 |
| Temp. Retention Time min. secs | | | | |
| Above 120° C. | 11.00 | 18.00 | 27.00 | 35.30 |
| Above 100° C. | 44.10 | 39.20 | 40.30 | 70.40 |
| Above 70° C. | 78.00 | 63.20 | 71.00 | 94.40 |

EXPERIMENTAL EXAMPLE 9

An additional agent for restraining heat generation was added to CaO. The amounts of the additional agent and water were varied and the temperature was measured using the vessel shown in FIG. 1. The temperature was measured around CaO.

TABLE 7

| No. | 1 | 2 | 3 | 4 | 5 | 6 | 7 | 8 | 9 |
|---|---|---|---|---|---|---|---|---|---|
| Quicklime (g) | 60 | 60 | 60 | 60 | 60 | 60 | 60 | 60 | 60 |
| Added Components (g) | 40 | 40 | 30 | 30 | 20 | 0 | 0 | 20 | 20 |
| Reaction Water (ml) | 19.2 | 32.0 | 32.0 | 25.0 | 32.0 | 32.0 | 32.0 | 32.0 | 32.0 |
| Highest Temp. (°C.) | 90.0 | 108.0 | 186.0 | 150.0 | 186.0 | 172.0 | 152.7 | 194.7 | 200.0 |
| Temp. Retention Time (mins. secs) | | | | | | | | | |
| Above 120° C. | — | — | 30.20 | 18.40 | 25.30 | 15.00 | 11.50 | 23.00 | 30.20 |
| Above 100° C. | — | 8.20 | 36.30 | 24.10 | 34.20 | 25.50 | 18.20 | 32.50 | 39.10 |
| Above 70° C. | 11.40 | 21.30 | 48.10 | 35.50 | 49.10 | 39.20 | 27.40 | 48.00 | 57.10 |
| Thermal Insulation Material (Layer) | — | — | — | — | — | — | — | 1 | 2 |
| Temperature Outside Thermal | — | — | — | — | — | — | — | 85 | 50 |

TABLE 7-continued

| No. | 1 | 2 | 3 | 4 | 5 | 6 | 7 | 8 | 9 |
|---|---|---|---|---|---|---|---|---|---|
| Insulation Material | | | | | | | | | |

EXPERIMENTAL EXAMPLE 10

The sterilizing effects on the four kinds of bacteria were tested using the vessel shown in FIG. 1.

The bacteria were suspended in water and a sterile gauze was soaked in the resulting solution. The gauze was placed in a chamber in the vessel. After closing the lid of the chamber, the safety seal was torn off by pulling a string, then the bacteria were killed by the reaction between 150 g of CaO and 50 ml of water. Then the gauze was placed in an incubator. The result showed that all of the four kinds of bacteria were completely destroyed.

What is claimed is:

1. A device for sterilization of medical waste, the device comprising an enclosure including:
   a first portion having a space receiving the medical waste;
   a second portion surrounding the first portion having a space containing a heat generating agent generating heat upon reaction with water, the space of the second portion being physically separated from the space of said first portion by a continuous, non-perforated partition capable of excluding passage of water and heat generating agent therethrough from the second portion to the first portion prior to chemical reaction between the heat generating agent and water;
   a third portion having a space containing a reactant containing water capable of exothermically reacting with the heat generating agent, the space of the third portion being physically separated from the space of said second portion;
   means for bringing said reactant containing water in the space of the third portion in contact with said heat generating agent in the space of the second portion so that an exothermic reaction is initiated to generate heat and steam by passage of the reactant containing water to the space of the second portion through a passage upon activation of said means; and
   whereby the heat and steam melt said partition between the first and second portions so that the medical waste in the first portion is subjected to the generated heat and steam.

2. A device for sterilization of medical waste in accordance with claim 1, wherein said heat generating agent in the second portion is iron powder.

3. A device for sterilization of medical waste in accordance with claim 1, wherein said reactant includes oxygen.

4. A device for sterilization of medical waste in accordance with claim 1, wherein said heat generating agent in said second portion is at least one compound selected from the group consisting of calcium oxide, calcined dolomite, and magnesium oxide.

5. A device for sterilization of medical waste in accordance with claim 1, wherein the reactant includes an aqueous solution.

6. A device for sterilization of medical waste in accordance with claim 1, wherein the reactant includes an aqueous slurry.

7. A device for sterilization of medical waste in accordance with claim 1, further comprising:
   a fourth portion having a space physically separated from the spaces of the first, second and third portions and containing a deflated expansion bag, the fourth portion being disposed in proximity to the first portion having space receiving the medical waste, and
   a connection pipe connecting the expansion bag to the space of said second portion so that expanded air and steam generated by the exothermic reaction can flow into the expansion bag through the connection pipe.

8. A device for sterilization of medical waste in accordance with claim 1, wherein said partition between the first and second portions comprises a material selected from the group consisting of polypropylene, polystyrene, and polyethylene.

9. A device for sterilization of medical waste in accordance with claim 1, wherein said first portion includes a medical waste disposal port having a hermetically sealing structure and said second portion includes an exhaust port for exhausting steam generated by the exothermic reaction of said heat generating agent and said reactant, the exhaust port having a microbe-barrier filter for preventing the escape of micro-organisms.

10. A device for sterilization of medical waste in accordance with claim 7, wherein said first portion includes a medical waste disposal port having a hermetically sealing structure so that the expanded air and steam generated by the exothermic reaction of said heat generating agent and said reactant do not substantially leak out of said device.

* * * * *